United States Patent
Palmers

(10) Patent No.: US 6,251,345 B1
(45) Date of Patent: *Jun. 26, 2001

(54) DEVICE FOR STERILIZING OF INSTRUMENTS

(75) Inventor: Goran Palmers, Askim (SE)

(73) Assignee: TSP Medical AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,605

(22) PCT Filed: Jun. 18, 1997

(86) PCT No.: PCT/SE97/01103

§ 371 Date: Dec. 17, 1998

§ 102(e) Date: Dec. 17, 1998

(87) PCT Pub. No.: WO97/48424

PCT Pub. Date: Dec. 24, 1997

(30) Foreign Application Priority Data

Jun. 18, 1996 (SE) .................................................. 9602409

(51) Int. Cl.⁷ ................................. A61L 2/07; A61L 2/16
(52) U.S. Cl. ........................... 422/300; 422/295; 422/297
(58) Field of Search .................................... 422/292, 295, 422/297, 298, 299, 300; 134/95.2, 95.3, 170, 171

(56) References Cited

U.S. PATENT DOCUMENTS

| 649,512 | * | 5/1900 | Goodwin | 422/300 |
| 891,758 | * | 6/1908 | Allspaw | 422/300 |
| 1,007,274 | * | 10/1911 | Dean | 422/300 |
| 1,228,464 | * | 6/1917 | Mazzei | 422/300 |
| 1,435,143 | * | 11/1922 | Bensman | 422/297 |
| 2,127,932 | * | 8/1938 | Pellkofer | 422/300 |
| 4,663,122 | * | 5/1987 | Sparks | 422/297 |
| 5,057,283 | * | 10/1991 | Guggenheim et al. | 134/171 |
| 5,197,499 | * | 3/1993 | Bodenmiller et al. | 134/95.2 |
| 5,552,113 | * | 9/1996 | Jennings | 422/297 |
| 5,723,090 | * | 3/1998 | Beerstecher et al. | 422/300 |

FOREIGN PATENT DOCUMENTS 25 28 901   12/1976   (DE) .
0638298     2/1995    (EP) .

* cited by examiner

Primary Examiner—Elizabeth McKane
(74) Attorney, Agent, or Firm—Merchant & Gould P.C.

(57) ABSTRACT

A device for sterilization of instruments, particularly dental instruments, in an autoclave provided with an instrument holder. The autoclave has an inlet and an outlet for different fluids, such as cleaning and rinsing liquids, and sterilization and maintenance media. The autoclave incorporates several gas-tight closable chambers each of which is equipped with at least one instrument holder. Each chamber and instrument holder is provided with an individually adjustable and controllable inlet and outlet for the fluids and media. Each chamber, as a result of the autoclaving process, defines a sterile package in the form of a closed storage vessel for at least one treatment instrument. The chambers are connected to a central unit for choosing a sterilization program, depending upon the exposure of the instrument outside the autoclave, as well as preparing and controlling the fluids and media.

6 Claims, 3 Drawing Sheets

DEVICE FOR STERILIZING OF INSTRUMENTS

The present invention relates to a device for sterilization of instruments particularly dental instruments, in an autoclave equipped with instrument holders, which autoclave has inlet and outlet for different fluids, such as cleaning and rinsing fluids, sterilization and maintenance media and the like.

BACKGROUND

The demands for medical and particularly dental equipment to be sterile has increased. To permit these instruments to be sterilized in a limited period of time, it is required that they are first cleaned so that germs and spores can not lay protected in contaminations left on the instruments. The efficiency of the cleaning is very much dependent on how long the instrument has been resting between use and cleaning.

An instrument is often sterilized in an impermeable package which prevents the instrument from being contaminated after sterilization. If the instrument is not packaged, it is only considered sterile until the sterilization equipment has been opened. Cleaning can not be effected in the packaged but the instruments have to be packed after the cleaning.

For instruments requiring several steps in the sterilization process it is not possible to have them packed during the entire process. If the instrument shall be both washed before the sterilization and lubricated after the sterilization, this must be solved in another manner.

Another method could be to refrain from picking out the instruments from the process chamber until they are to be used. As sterilizers are large apparatuses positioned in separate rooms and which sterilize several instruments at the same time this will not work out satisfactorily.

EP-A1-0 638 298 discloses a cassette for hygienic treatment of dental instruments in a pressure-proof sealable chamber. The cassette incorporates a number of adapters as holders for the instruments, which adapters are connected to conduits for cleaning and washing the interior of the instruments with the aid of treatment media. The exterior of the instruments is treated with treatment media which is sprayed thereon by nozzle equipped tubes that project into cassette. In the conduits for the treatment media are provided magnetic valves, which open and close by means of a micro processor. The treatment time is about 30 minutes. The design of the apparatus with a cassette and a number of adapters and the length of the treatment time means, that the apparatus has to be used for several patients, which means, that as soon as the cassette has been opened for one patient, the remaining instruments do not longer fulfil the demands for sterility. The rather big sterilizing capacity of the apparatus furthermore means, that it might take some time before the next hygienic treatment can be effected, with the consequence that the instrument have been exposed during different long times and therefore should need different treatment times or that all instruments always are treated during a time of excessive length, in order to avoid that strains of germs have survived.

SUMMARY OF THE INVENTION

The purpose of the invention is to provide a device, which means:

that all uncertainty about poor sterility is set aside, that every instrument or group of instruments are treated during the time required with reference to its exposure in non-sterile surroundings in order to achieve high demands on sterility, that the time for autoclave treatment is short, e.g. only five minutes, without renouncing on the quality of the sterilization, that no contamination of the instruments by instruments intended for other patients takes place when removed from the autoclave, that the instruments for every individual patient are packed in a sterile manner up until they are needed, and that the quality security is guaranteed.

These tasks have been solved in an autoclave that incorporates several separate gas-tight closable chambers each being equipped with at least one instrument holder, each chamber and instrument holder is provided with an individually adjustable and controllable inlet and outlet for the fluids and media, each chamber after the autoclave treatment is a sterile package in the form of a closed storage vessel container for at least one instrument, intended for treatment of only one patient and the chambers are connected to a central unit for choice on one hand of a sterilization program dependent on the exposure of the instruments outside the autoclave, and on the other hand preparation and control of the fluids and media and recording of treatment steps taken and possibly treatment and waiting times in the different chambers.

The device and its central unit controls all phases required for having the instruments cleaned, sterilized and if required lubricated, so that they are ready for use, whereby the routines of treatment shall be so simple that it is almost independent of human errors. The device is preferably positioned in the room where the instruments shall be used. The device then simultaneously will form a sterile package for the instruments, until they are to be used.

When, a sterilized instrument is needed, the chamber is opened which contains the instrument needed. The other instruments are still sterile in their different sterilization chambers. When he has used an instrument it is returned to the chamber, which is closed. The chamber then can not be opened until the cleaning and sterilization process is finished. For certain simple and cheap instruments, which are not subjected to wear by the sterilization, it is possible to have several instruments in the same chamber. Then it is necessary to sterilize also the unused instruments as soon as anyone of them has been used, This means that the instruments will not lay around dirty for a long period of time. At normal handling the instruments is placed on a tray, which is then sent to the sterilization room. The time between the use and the cleaning is difficult to control and it is dependent on how the routines are followed. If the instrument will lay around unwashed for a long period of time is it possible that a more thorough process is required for getting it clean and sterile.

If every instrument has an individual marking, which can be sensed when the instrument is in its position in the chamber, it is possible to get an excellent quality control system. It is possible to see that the correct instrument is positioned in the correct chamber, to control for how long an instrument has been outside a chamber, and it is possible to record how many times an instrument has been used. With this information is it possible to control the process to give a perfectly satisfactory result without requiring unnecessary long time.

Examples of such a marking can be a pin code. It can be read when the instrument is pushed into the chamber or when the chamber is closed. An advantage is that the patient can see himself that only acceptably sterilized instruments are used during the treatment.

DESCRIPTION OF THE DRAWINGS

Hereinafter the invention will be further described as an embodiment with reference to the accompanying drawings.

DESCRIPTION OF EMBODIMENTS

Figure 1:
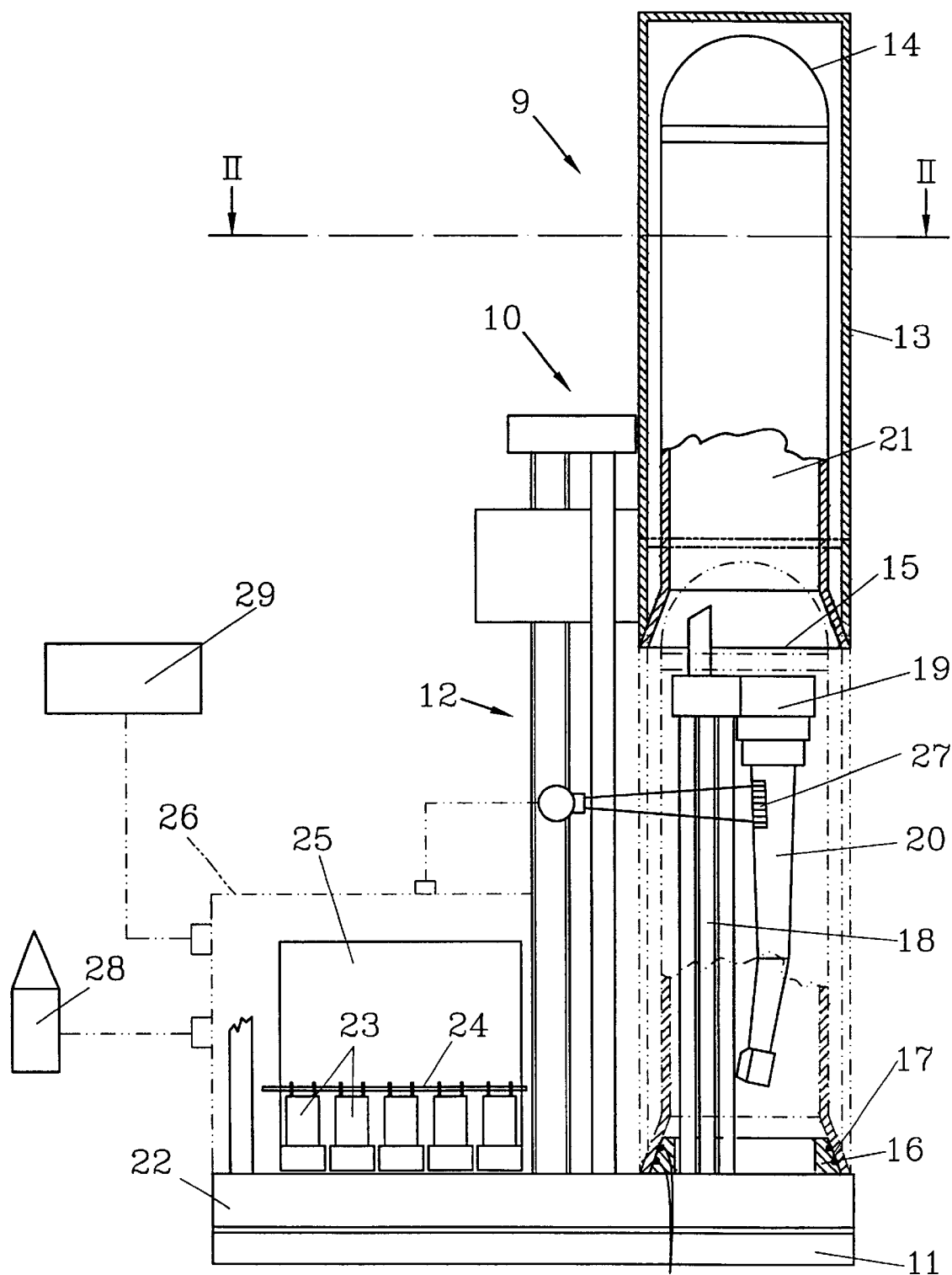
FIG. 1 shows a side view of a sterilization device according to the invention and forming part of an autoclave.
Figure 2:
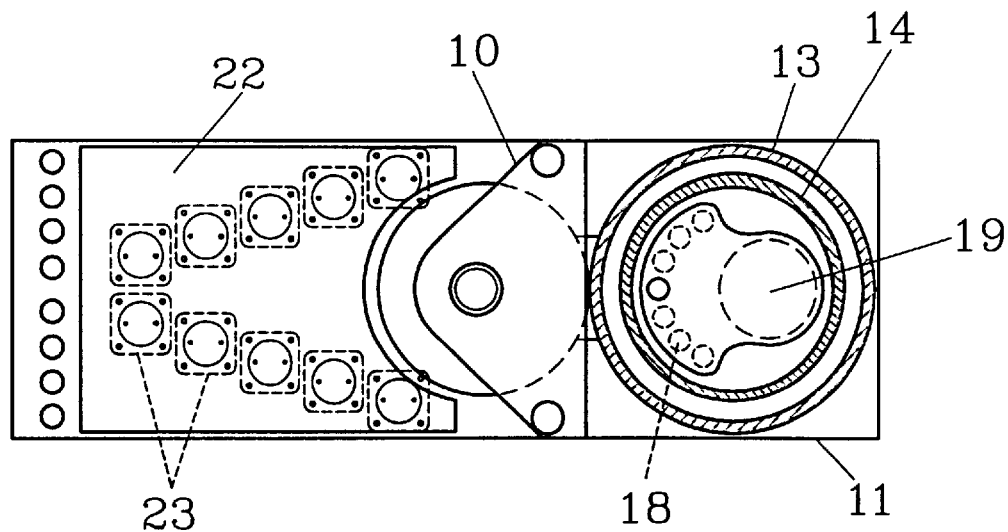
FIG. 2 shows the sterilization device according to FIG. 1 in a view from above.
Figure 4:
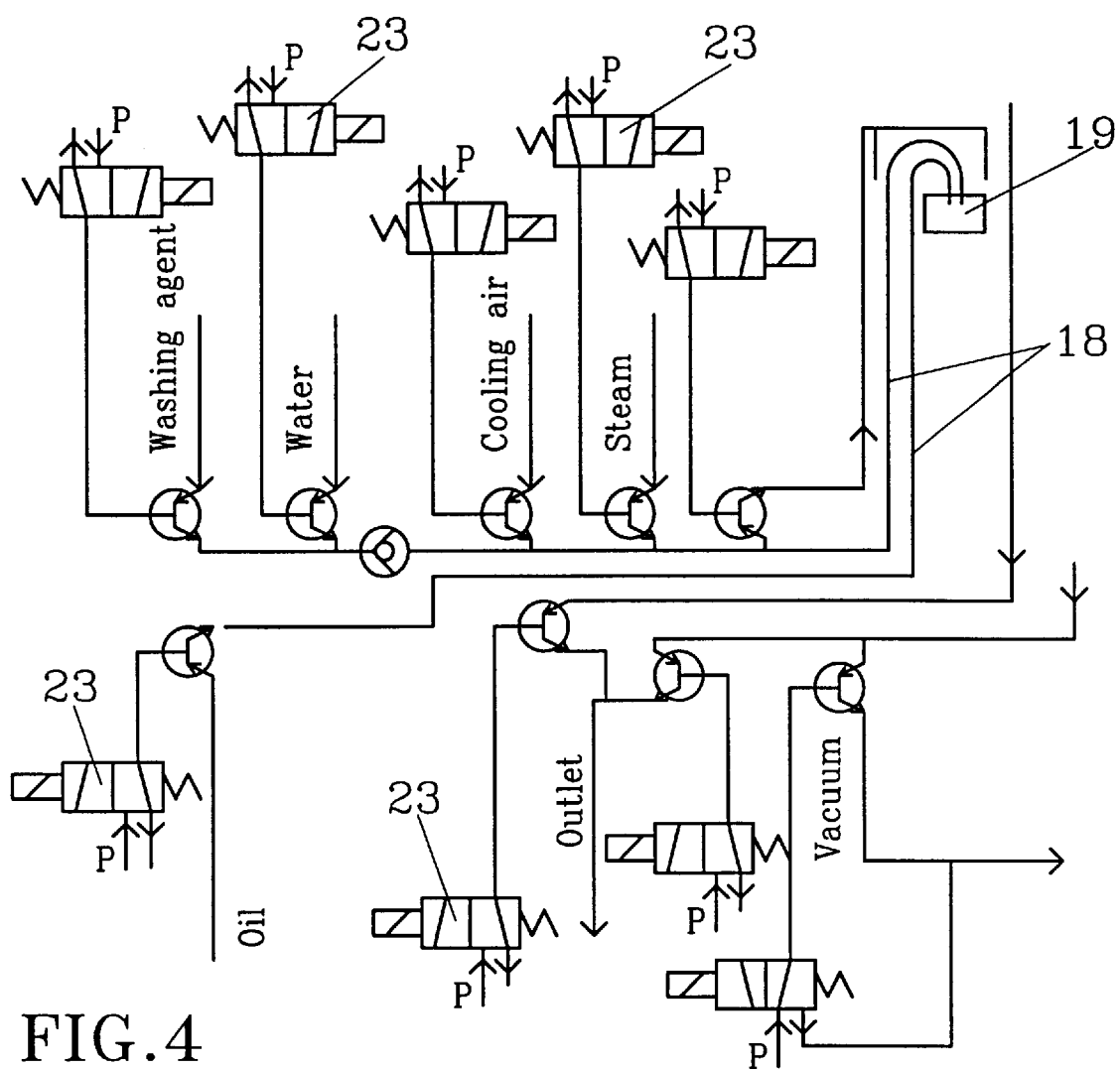
FIG. 4 shows a coupling diagram over the supply and discharge of the fluids and media.

The device according to the invention incorporates an autoclave 9, a base plate 11, on which is vertically mounted a pillar stand 10 with an actuator 12, e.g. a ball screw mechanism. This supports a vertically adjustable, cylindrical outer casing 13, and an inner casing 14 situated inside this, which both together form an inverted, highly insulated chamber 21 having vacuum as insulation between the casings. At the lower end of the chamber there is an opening 15. On the base plate 11 is provided a seating 16 having seals 30, which can be interconnected in a gas- and liquid-tight manner with the inner tapering sealing surface 17 of the casing 14 at the opening 15. Inside the seating 16 is fixedly arranged a vertical pillar 18, which at its free, upper portion is provided with a connecting member 19, for connection of at least one instrument 20, e.g. an angled hand piece of a dental drilling unit. The casing 14 is dimensioned and designed so that it can be positioned by the actuator 12 and over the pillar 18 the instrument 20 and make a sealing engagement against the seating 16, thereby forming a gas-tight and fluid-tight sterilization chamber 21 about the instrument or instruments.

On the base plate 11 is mounted a valve block 22, for all valves 23 forming part of the system, and which are controlled by means of a central unit 26 via a printed board 24. The valves 23 control the inlet and outlet of different fluids, such as water, pressurized air, steam, cleaning agent, vacuum and lubricant, etcetera, which via a system of conduits in the valve block are led into the sterilization chamber 21, either directly into the instrument via the pillar 18 and the connection member 19 and/or into the space between the casing 14 and the instrument 20. In the base plate are arranged outlet openings for draining the chamber 21.

Figure 3:
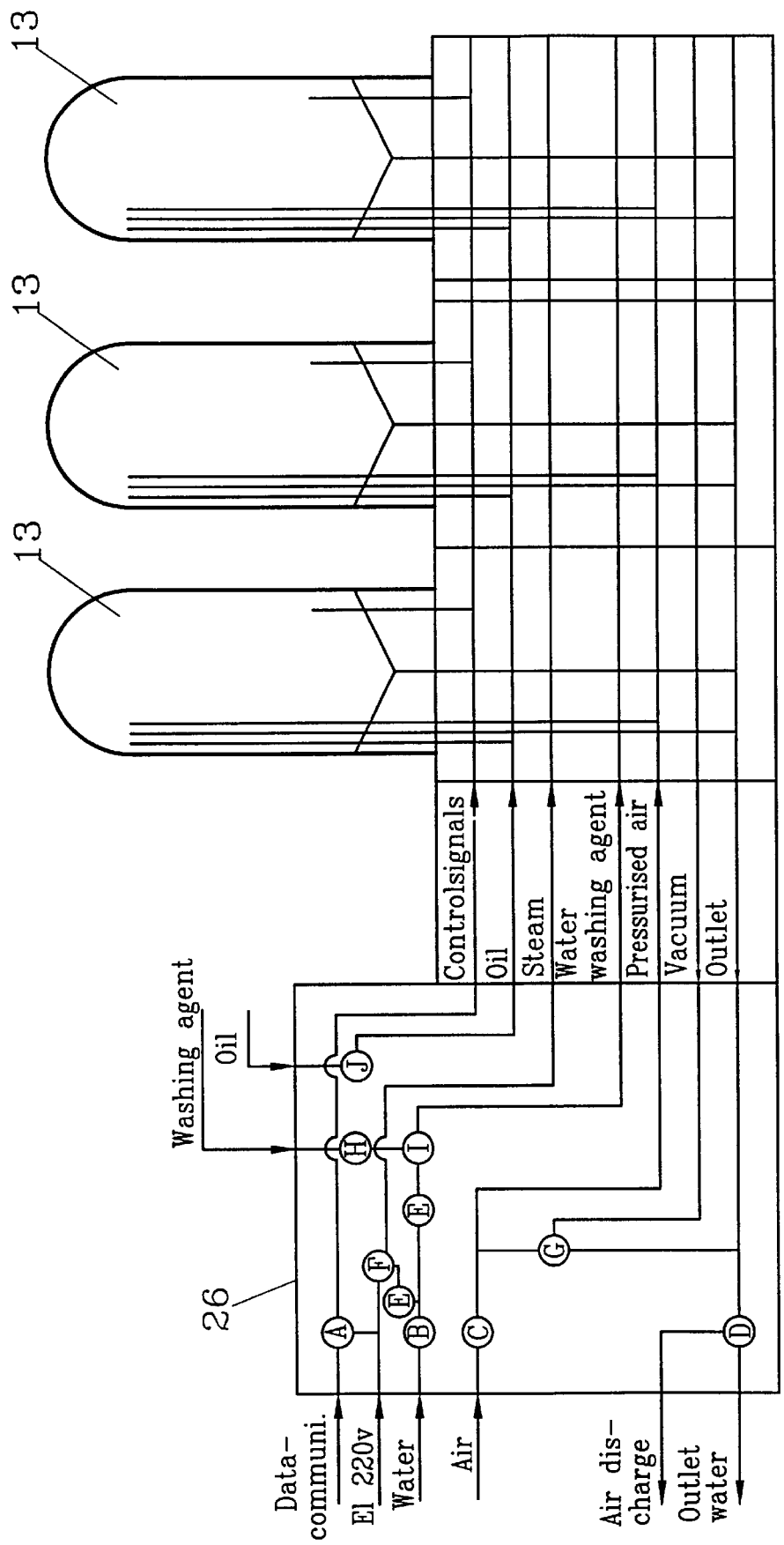
FIG. 3 shows a principal diagram of an autoclave with several sterilization devices connected to a common central unit.

In the central unit 26, which is arranged on the base plate 22 is mounted a steam generation apparatus (not shown). The central unit 26 also incorporates a micro processor 25, which controls the sterilization procedure in accordance with a chosen program and which adjusts the dosing of different fluids. In FIG. 3 is schematically illustrated how the conduits for the different fluids and the outlet conduits are arranged. Letters A–J refer to different functions. The micro processor 25, which also has a memory function, is designed so, that it measures the time during which the instrument is removed and adapts the cleaning program in view thereof. The longer time which has elapsed since the sterile instrument has been removed from the chamber, the longer time is required for the cleaning procedure.

The instruments are provided with an identification code 27, e.g. a pin code or the like, which makes it possible to keep track of firstly where—in which chamber—the instrument is positioned for the moment, secondly how often it has been used and thirdly—if the processor is equipped with an input unit, by which the patient case-book can be combined with the data obtained from the device according to the invention—for which patient it has been used and when. A pin code reader (not shown) is provided for transferring the code to the processor. These data are necessary firstly for a rational handling of the instruments, as it is not possible to look for a certain instrument in different chambers, as the sterility then would have become broken, and secondly is it possible to have statistics over the frequency of use and thereby it is possible to supervise service and maintenance, and thirdly it is possible to enter data over which instruments, that have been used for a certain patient in the patient case-book in the computer. The last mentioned data can also be a basis for charging the treatment costs.

It also is possible, that every instrument—e.g. the angled hand piece 20—and its connecting member 19 are not interchangeable, i.e. a certain instrument matches only a specific connecting member, thus the same instrument is always treated and stored in a certain autoclave. Therefore mix-ups are precluded, as the instrument always is in the same position.

The micro processor 25 of the central unit, which can be a full scale computer can also have a printer 29 associated therewith, and by means of which information from the patient case-book and data about finished treatment can be printed out and debited.

The invention is not limited to the embodiments shown and described but can be varied within the scope of the claims. Thus the sterilization of the instruments can be effected in another arbitrary position, e.g. in a horizontal position, the pillar 18 can be excluded and the connecting member can be mounted directly on the base plate.

What is claimed is:

1. A device for sterilization of instruments, comprising:
    an autoclave provided with a plurality of instrument holders, said autoclave having an inlet and an outlet for different fluids:
    wherein the autoclave includes a plurality of casings that define a plurality of gas-tight closable chambers each of which is sized to enclose at least one of said instrument holders; and
    wherein said casings and said instrument holders are each provided with individual adjustable and controllable inlets and outlets in flow communication with said autoclave inlet and outlet;
    wherein each chamber defines a sterile closed storage vessel for at least one of said instruments, and the chambers are connected to a central unit for choice of one of a sterilization program dependent on the exposure of the instrument outside the autoclave, preparation and control of said fluids, recordal of treatment steps made, and treatment and waiting times in the different chambers.

2. A device as claimed in claim 1, further including a connecting member associated with each said chamber for mounting of an instrument, said connecting member fluidly connecting the instrument to said fluids.

3. A device as claimed in claim 2,
    wherein the central unit includes a micro processor having a memory function for recordal of the presence and absence of the instrument associated with each said chamber.

4. A device as claimed in claim 3, wherein each instrument is provided with an identification code, and further comprising an identification device for reading or sensing the identification code.

5. A device as claimed in claim 3, wherein the central unit comprises a computer equipped with an input and logging equipment for recordal of data.

6. A device as claimed in claim 1, further comprising a base plate that supports each said casing, said base plate is provided with a plurality of seatings for liquid-tight connection with a respective one of said casings, and said casings are vertically adjustable.

* * * * *